United States Patent [19]

Jarque et al.

[11] 4,145,424
[45] Mar. 20, 1979

[54] 1,4,4A-TRIMETHYL-1,2,4A,-4B,9A,10A-HEXAHYDRO-10H-BENZO [b] THIENO [2',3':4,3]CYCLOPENT-[1,2-b]-PYRIDINE

[75] Inventors: Ricardo G. Jarque, Barcelona; Mercedes A. Domingo, San Juan Despi; Juan Bosch Cartes, Barcelona; Cristobal M. Roldan; Fernando R. Peinado, both of Madrid, all of Spain

[73] Assignee: Laboratorios Made, S.A., Madrid, Spain

[21] Appl. No.: 886,501

[22] Filed: Mar. 14, 1978

[30] Foreign Application Priority Data

Apr. 14, 1977 [ES] Spain ................................. 457.778

[51] Int. Cl.² ...................... A61K 31/44; C07D 521/00
[52] U.S. Cl. ........................................ 424/256; 546/62
[58] Field of Search ................. 260/294.8 A, 290.54, 260/290.55; 424/256

[56] References Cited

U.S. PATENT DOCUMENTS

| 3,320,265 | 5/1967 | Clarke | 260/293.54 |
| 3,417,094 | 12/1968 | Dexter | 260/293.54 |

*Primary Examiner*—Alan L. Rotman
*Attorney, Agent, or Firm*—Ladas, Parry, Von Gehr, Goldsmith & Deschamps

[57] ABSTRACT

The compound 1,4,4a-trimethyl-1,2,4a,4b,9a,10a-hexahydro-10H benzo [b] thieno [2',3':4,3] cyclopent [1,2-b]-pyridine of the formula:

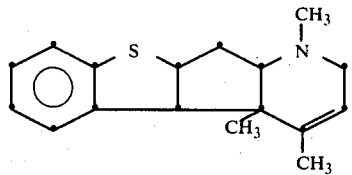

or a pharmaceutically acceptable acid addition salt thereof is disclosed as an analgesic compound.

2 Claims, No Drawings

1,4,4A-TRIMETHYL-1,2,4A,-4B,9A,10A-HEXAHYDRO-10H-BENZO [b] THIENO [2',3':4,3]CYCLOPENT-[1,2-b]-PYRIDINE

The present invention relates to the preparation of 1,4,4a-trimethyl-1,2,4a,4b,9a,10a-hexahydro-10H-benzo[b]thieno[2',3':4,3]cyclopent [1,2-b]pyridine of formula I

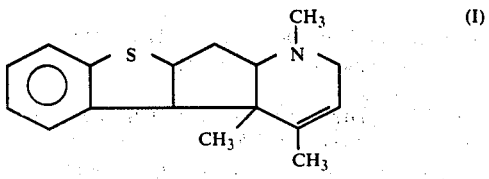

and to the preparation of the addition salts thereof with pharmacologically acceptable acids, as well as to pharmaceutical composition containing same along with a pharmaceutically acceptable inert carrier for example halohydrides, starting from 2-(2-benzo[b]thienylmethyl-1,3,4-trimethyl-1,2,5,6-tetrahydropyridine, of formula II, which compound was described in the Spanish Patent Application No. 456.282, where a process for preparing it is also described.

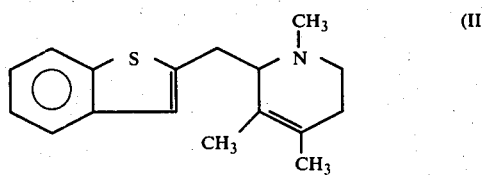

The mentioned compound I is a new substance, of interest as an analgesic, which is prepared according to the process of the invention by reacting compound II with a Lewis acid, for example aluminium bromide, at the reflux temperature of carbon disulphide.

Upon completion of the reaction, the mixture is cooled, rendered alkaline with concentrated ammonium hydroxide and extracted with ether, yielding an oil from which 1,4,4a-trimethyl-1,2,4a,4b,9a,10a-hexahydro-10H-benzo[b]thieno-[2',3':4,3]cyclopent [1,2-b]pyridine (I) is separated by silica gel column chromatography. If desired, this compound is converted into its hydrochloride.

The following example is given by way of illustration only and in no way is it to be considered as limiting the scope of the invention.

EXAMPLE: PREPARATION OF 1,4,4a-TRIMETHYL-1,2,4a,4b,9a,10a-hexahydro-10H-benzo[b]thieno[2',3':4,3]cyclopent [1,2-b]-pyridine (I).

10.2 g. of 2-(2-benzo[b]thienylmethyl)-1,3,4-trimethyl-1,2,5,6-tetrahydropyridine hydrochloride (II) are suspended in 100 ml. of carbon disulfide. The slurry is stirred, slowly adding 19.3 g. of aluminum tribromide. The mixture is heated under reflux for 20 hours, left to cool, poured over ice and water, rendered alkaline with ammonium hydroxide, extracted with ether and dried with anhydrous magnesium sulphate. Once the ether is evaporated there is obtained an oil which is chrommatographed through a silica gel column. The fractions eluted with 60:40 benzene:chloroform yield 1.8 g. of 1,4,4a-trimethyl-1,2,4a,4b,9a,10a-hexahydro-10H-benzo[b]-thieno[2',3':4,3]cyclopent [1,2-b]pyridine (I). Melting point 179°–180° C. (ethanol).

Analysis calculated for $C_{17}H_{21}NS$: C,75.27; H,7.74; N,5.16; S,11.82. Found: C,74.80; H,7.98; N,5.39; S,11.53.

The hydrochloride is obtained with a melting point of 275°–280° C. (acetone-methanol).

PHARMACOLOGICAL PROPERTIES OF THE PRODUCTS OF THE INVENTION PRODUCTS

I:- 1,4,4a-trimethyl-1,2,4a,4b,9a,10a-hexahydro-10H-benzo-[b]thieno[2',3':4,3]cyclopent [1,2-b]pyridine.

II:- 2-(2-benzo[b]thienylmethyl-1,3,4-trimethyl-1,2,5,6-tetrahydropyridine.

They are products with analgesic activity. Their toxicity and activity have been compared with those of dextropropoxyphene.

A — ACUTE TOXICITY

Acute toxicity studies were performed on I.C.R. Swiss albino mice, of both sexes, weighing 30 ± 2 g, kept fasting for 24 hours prior to the experiment. The room temperature and relative humidity were kept constant. The products were administered intraperitoneally, counting the number of deaths 48 hours after the treatment. The calculation of the lethal dose ($LD_{50}$) was made with the Litchfield-Wilcoxon test. The results obtained were:

TABLE I

| Products | $LD_{50}$ (mg/kg) |
|---|---|
| I | 232.9 |
| II | 129.1 |
| Dextropropoxyphene | 140 |

B - ANALGESIC ACTIVITY

1. Thermal analgesia

The thermal analgesic effect was studied on I.C.R. Swiss albino mice. The hot plate technique was used at 55° C. Batches of 10 mice were made.

The products under study were administered intraperitoneally and after 30 minutes the mice were placed on the hot plate, counting the number of seconds they took to jump. Batches of control animals which were only injected with distilled water are used.

The results were given in tables 2 and 3.

TABLE II

| Treatment | Dose | Jumping time in sec. $\bar{x}$ ± S.E.M. (1) | Significance of differences Controls | Dextropropoxyphene |
|---|---|---|---|---|
| Control | — | 64.1 ± 10.308 | — | — |
| Dextropropoxyphene | 50mg/kg | 119.2 ± 18.852 | $p<0.02$ | — |
| I | 50mg/kg | 114.5 ± 9.771 | $p<0.005$ | N.S. |

(1) Mean values ± standard error of the mean.

Product I has the same analgesic activity as dextropropoxyphene.

TABLE III

| Treatment | Dose | Jumping time in sec. $\bar{x}$ ± S.E.M. (1) | Significance of differences Controls | Dextropropoxyphene |
|---|---|---|---|---|
| Control | — | 41.1 ± 5.284 | — | — |
| II | 30mg/kg | 36.4 ± 6.199 | N.S. | $p<0.02$ |
| Dextropropoxyphene | 30mg/kg | 60 ± 6.119 | $p<0.05$ | — |

Product II is lacking analgesic activity.

2. Chemical analgesia

The analgesic effect was studied on I.C.R. Swiss albino mice with the acetic acid writhing technique. Batches of 10 mice were made.

The products under study were administered intraperitoneally and after 30 minutes 0.25 ml of 1% acetic acid are injected intraperitoneally. A batch of control animals which only receive acetic acid is used. The number of writhes in each mouse is counted 20 minutes after administration of the acetic acid.

The results are given in tables 4 and 5.

TABLE IV

| Treatment | Dose | No. of writhes $\bar{x} \pm$ S.E.M. | Significance of differences with Controls | Dextropropoxyphene |
|---|---|---|---|---|
| Control | — | 113.7 ± 5.086 | — | — |
| Dextropropoxyphene | 25mg/kg | 55 ± 10.098 | p<0.00005 | — |
| I | 25mg/kg | 74.22 ± 9.714 | p<0.002 | N.S. |

Product I has the same analgesic activity as dextropropoxyphene.

TABLE V

| Treatment | Dose | No. of writhes $\bar{x} \pm$ S.E.M. | Significance of differences with Controls | Dextropropoxyphene |
|---|---|---|---|---|
| Control | — | 143.37 ± 12.56 | — | — |
| Dextropropoxyphene | 30mg/kg | 42.8 ± 6.26 | p<0.00005 | — |
| II | 30mg/kg | 109.7 + 6.47 | p<0.05 | p<0.00005 |

Product II has analgesic activity which is significantly less than that of dextropropoxyphene.

We claim:

1. The compound 1,4,4a-trimethyl-1,2,4a,4b,9a,10a-hexahydro-10H-benzo [b] thieno [2',3':4,3]-cyclopent [1,2-b] pyridine (I) or a pharmaceutically acceptable acid addition salt thereof.

2. A pharmaceutical composition containing a pharmaceutically effective amount of the product of claim 1 as active ingredient along with a pharmaceutically acceptable inert carrier.

* * * * *